(12) United States Patent
Tavares et al.

(10) Patent No.: US 9,914,071 B2
(45) Date of Patent: Mar. 13, 2018

(54) SYSTEMS AND METHODS FOR SEPARATING AND PURIFYING BUTADIENE

(71) Applicant: Braskem S.A., Camacari—BA (BR)

(72) Inventors: Luiz Felipe de Souza Tavares, Rio de Janeiro (BR); Bruno Maia Moreira, Rio de Janeiro (BR); Roberto Werneck Do Carmo, Rio de Janeiro (BR); Paulo Luiz de Andrade Coutinho, Rio de Janeiro (BR)

(73) Assignee: Braskem S.A., Camacari—BA (BR)

( * ) Notice: Subject to any disclaimer, the term of this patent is extended or adjusted under 35 U.S.C. 154(b) by 272 days.

(21) Appl. No.: 14/761,551

(22) PCT Filed: Jan. 30, 2014

(86) PCT No.: PCT/BR2014/000024
§ 371 (c)(1),
(2) Date: Jul. 16, 2015

(87) PCT Pub. No.: WO2014/121357
PCT Pub. Date: Aug. 14, 2014

(65) Prior Publication Data
US 2015/0352461 A1 Dec. 10, 2015

Related U.S. Application Data

(60) Provisional application No. 61/762,110, filed on Feb. 7, 2013.

(51) Int. Cl.
*B01D 3/14* (2006.01)
*C07C 7/04* (2006.01)
*C07C 7/12* (2006.01)

(52) U.S. Cl.
CPC ............... *B01D 3/143* (2013.01); *C07C 7/04* (2013.01); *C07C 7/12* (2013.01)

(58) Field of Classification Search
CPC .............. B01D 3/143; C07C 7/04; C07C 7/12
See application file for complete search history.

(56) References Cited

U.S. PATENT DOCUMENTS

| 5,849,970 | A | 12/1998 | Fall et al. |
| 8,128,826 | B2 | 3/2012 | Plante et al. |
| 2011/0046422 | A1* | 2/2011 | McAuliffe ............... C10L 1/04 585/16 |

FOREIGN PATENT DOCUMENTS

| DE | 19838449 | * 3/2000 | ............ C07C 41/42 |
| GB | 1122673 | 8/1968 | |

(Continued)

*Primary Examiner* — In Suk C Bullock
*Assistant Examiner* — Youngsul Jeong
(74) *Attorney, Agent, or Firm* — K&L Gates LLP (57) ABSTRACT

The present disclosure generally relates to systems for isolating and/or purifying byproducts of anaerobic fermentation processes, and methods of using same. In one embodiment, gas compositions comprising conjugated diolefins (e.g., 1,3-biobutadiene and/or isoprene) and various amounts of impurities (e.g., water vapor from fermentation media, carbon dioxide from microbe respiration, and organic bio-byproducts such as propanol) are produced in a fermentation process. In some embodiments, the system includes one or more compressors and/or one or more distillers suitable for low-temperature separation of the conjugated olefin(s) from a substantial amount of the impurities in the gas composition.

22 Claims, 3 Drawing Sheets

(56) References Cited

FOREIGN PATENT DOCUMENTS

| KR | 100806672 B1 * | 2/2008 | ............. C07C 13/18 |
|----|----------------|--------|--------------------------|
| WO | 2010099201 | 9/2010 | |
| WO | 2011075534 | 6/2011 | |
| WO | WO2011075534 A2 * | 6/2011 | ................ C08F 6/12 |

* cited by examiner

SYSTEMS AND METHODS FOR SEPARATING AND PURIFYING BUTADIENE

PRIORITY CLAIM

This application is a 371 National Stage Application of International Application No. PCT/BR2014/000024, filed Jan. 30, 2014, which claims priority to and the benefit of U.S. Application Ser. No. 61/762,110, filed on Feb. 7, 2013 the disclosures of each of which are incorporated by reference herein in their entireties.

BACKGROUND

Butadiene (1,3-butadiene, $CH_2=CH-CH=CH_2$, CAS 106-99-0) is a linear, conjugated 4-carbon hydrocarbon typically manufactured (along with other 4-carbon molecules) by steam cracking petroleum-based hydrocarbons. This process involves harsh conditions and high temperatures (at least about 850 C.). Other methods of butadiene production involve toxic and/or expensive catalysts, highly flammable and/or gaseous carbon sources, and high temperatures. Globally, several million tons of butadiene-containing polymers are produced annually. Butadiene can be polymerized to form polybutadiene, or reacted with hydrogen cyanide (prussic acid) in the presence of a nickel catalyst to form adiponitrile, a precursor to nylon. More commonly, however, butadiene is polymerized with other olefins to form copolymers such as acrylonitrile-butadiene-styrene (ABS), acrylonitrile-butadiene (ABR), or styrene-butadiene (SBR) copolymers.

The diminishing total reserve of petroleum and growing concerns about supply security and climate change have intensified interests to produce alternative renewable carbon sources to supplant oil-based carbon sources for fuels, thermoplastics, etc. The most common alternative renewable carbon source in use today is ethanol, which reached 6.5 billion gallons in production in the US in 2007. Ethanol fermented from starch or sugar feedstocks is commonly added as a component to gasoline to control combustion and increase the octane rating of the fuel. Ethanol can also be dehydrated to ethylene for polyolefin production.

Other approaches involve the utilization of naturally occurring fats and oils to produce bio-diesel, bio-naptha, or bio-propane. One approach, described in EP 5249689, involves removing the major part of the non-triglyceride and non-fatty acid components, thereby obtaining refined oils. The oils can be fractionated, alkyl-esters can be transformed into bio-diesel by a transesterification or into linear paraffins such as the bio-naphtha. Other approaches involve the transesterification of waste oil and fat triglycerides with a short chain alcohol such as methanol to form fatty acid methyl esters (FAME).

While these approaches have some promise, the supply of raw materials for production will become a challenge as demand increases, making a process that uses more abundant feedstocks, such as lignocellulose or other naturally occurring sugar sources, more attractive.

Recently, efforts have been made to develop new processes for producing advanced biofuels. For example, fermentation can be used to produce higher chain alcohols ($C_3$-$C_5$) which contain a high energy density, and are compatible with the current infrastructure as they are less hygroscopic. These alcohols (e.g., isopropanol, 1-propanol, 1-butanol, isobutanol, 3-methyl-1-butanol, 2-methyl-1-butanol, isopentenol) also can be dehydrated to alkenes, which can be esterified, hydrogenated, or polymerized to yield a variety of compounds that can be used as fuels, fuel additives, or other commodity chemicals.

While a wide variety of commercial products can be manufactured by fermentation processes, there remain many challenges for recovery and purification of useful chemicals. For example, WO/2011/075534 discloses steps of solvent extraction to purify isoprene. While this process appears to work, it is limited to aerobic fermentation byproducts, where isoprene or butadiene streams contain significant amounts of nitrogen and oxygen.

The methods and systems disclosed herein are optimized to isolate and/or purify byproducts produced using anaerobic fermentation processes. These may result in 1,3-biobutadiene gas compositions containing various amounts of impurities as part of the fermentation process (e.g., water vapor from the fermentation media, carbon dioxide as a respiration product, as well as other organic bio-byproducts such as propanol). The inventive process and systems herein have the advantage of utilizing compression and distillation steps under low temperatures. The invention is also applicable for other conjugated diolefins such as isoprene.

SUMMARY

The invention disclosed herein is directed to a system for separating and purifying a conjugated diolefin produced by fermentation under anaerobic conditions from a fermenter off-gas, and a method of use thereof comprising the steps of: a) obtaining a fermenter off-gas comprising the conjugated diolefin, a volatile impurity, a bio-byproduct impurity and water vapor; b) compressing the fermenter off-gas in a multi-stage compression system to produce a compressed stream; c) feeding the compressed stream into a first distillation zone for the removal of bio-byproduct impurity and water vapor, the first distillation zone having an upper reflux stage, middle distillation stages and a lower reboiler stage; d) contacting an overhead vapor stream produced from the bio-byproduct impurity and water removal distillation zone with an adsorbent to produce a dried overhead stream; e) feeding the dried overhead stream into a second distillation zone for the removal of volatile impurity by the top, with the second distillation zone having an upper reflux stage, middle distillation stages and a lower reboiler stage; and f) collecting at the bottom of the distillation zone for the removal of volatile impurity the resulting purified liquid conjugated diolefin.

In one embodiment of the invention, the conjugated diolefin comprises a compound selected from the group consisting of 1,3-butadiene and isoprene.

In another embodiment of the invention, the volatile impurity comprises a compound selected from the group consisting of $H_2O$ and $CO_2$.

In another embodiment of the invention, the volatile impurity comprises about 30 to about 80 mol % $CO_2$, and about 1 to about 20 mol % $H_2O$.

In another embodiment of the invention, the volatile impurity comprises about 45 to about 70 mol % $CO_2$.

In another embodiment of the invention, the bio-byproduct impurity comprises a polar impurity.

In another embodiment of the invention, the bio-byproduct impurity comprises a compound selected from the group consisting of ethanol, acetone, methanol, acetaldehyde, methacrolein, methyl vinyl ketone, 3-methylfuran, 2-methyl-2-vinyloxirane, cis- and trans-3-methyl-1,3-pentadiene, a $C_5$ prenyl alcohol (such as 3-methyl-3-buten-1-ol or 3-methyl-2-buten-1-ol), 2-heptanone, 6-methyl-5-hepten-2- one, 2,4,5-trimethylpyridine, 2,3,5-trimethylpyrazine, citronellal, methanethiol, methyl acetate, 1-propanol, diacetyl, 2-butanone, 2-methyl-3-buten-2-ol, ethyl acetate, 2-methyl-1-propanol, 3-methyl-1-butanal, 3-methyl-2-butanone, 1-butanol, 2-pentanone, 3-methyl-1-butanol, ethyl isobutyrate, 3-methyl-2-butenal, butyl acetate, 3-methylbutyl acetate, 3-methyl-3-buten-1-yl acetate, 3-methyl-2-buten-1-yl acetate, (E)-3,7-dimethyl-1,3,6-octatriene, (Z)-3,7-dimethyl-1,3,6-octatriene, (E,E)-3,7,11-trimethyl-1,3,6,10-dodecatraene, (E)-7,11-dimethyl-3-methylene-1,6,10-dodecatriene, 3-hexen-1-ol, 3-hexen-1-yl acetate, limonene, geraniol (trans-3,7-dimethyl-2,6-octadien-1-ol), and citronellol (3,7-dimethyl-6-octen-1-ol).

In another embodiment of the invention, the amount of bio-byproduct impurity relative to the amount of the conjugated diolefin in the fermenter off-gas is greater than about 0.01% by weight.

In another embodiment of the invention, the amount of bio-byproduct impurity relative to the amount of the conjugated diolefin in the fermenter off-gas is greater than about 0.5% by weight.

In another embodiment of the invention, the purified conjugated diolefin is further purified with an adsorption system.

In another embodiment of the invention, the adsorption system comprises activated carbon, alumina, silica, or Selexsorb® (BASF Chemical Company).

In another embodiment of the invention, the purified conjugated diolefin composition has a purity greater than about 90%.

In another embodiment of the invention, the purified conjugated diolefin composition has a purity greater than about 99%.

In another embodiment of the invention, the fermenter off-gas stream exits the compression system at a pressure of from about 6 bar to about 30 bar.

In another embodiment of the invention, the fermenter off-gas stream exits the compression system at a pressure of from about 9 bar to about 18 bar.

In another embodiment of the invention, the distillation zone for the removal of bio-byproduct impurity and water has an upper reflux stage, a lower reboiler stage, and middle distillation stages comprising about 1 to about 25 theoretical stages.

In another embodiment of the invention, the distillation zone for the removal of bio-byproduct impurity and water has an upper reflux stage, a lower reboiler stage, and middle distillation stages comprising about 3 to about 12 theoretical stages.

In another embodiment of the invention, the distillation zone for the removal of bio-byproduct impurity and water has no lower reboiler stage, comprising only an upper reflux stage and middle distillation stages comprising about 3 to about 12 theoretical stages.

In yet another embodiment of the invention is a system for separating and purifying a conjugated diolefin produced by fermentation under anaerobic conditions from a fermenter off-gas and a method of use thereof comprising the steps of: a) obtaining a fermenter off-gas comprising the conjugated diolefin, a volatile impurity, a bio-byproduct impurity and water vapor; b) compressing the fermenter off-gas in a multi-stage compression system; c) contacting the overhead vapor stream from a bio-byproduct impurity and water removal distillation zone with an adsorbent to produce a dried stream; d) feeding the dried stream into a distillation zone having an upper reflux stage, one or more middle distillation stages and a lower reboiler stage, wherein the volatile impurity is removed from the upper reflux stage; and e) collecting the resulting purified liquid conjugated diolefin at the lower reboiler stage.

In yet another embodiment of the invention, the distillation zone for the removal of volatile impurity has an upper reflux stage, a lower reboiler stage, and one or more middle distillation stages comprising about 1 to about 25 theoretical stages.

In yet another embodiment of the invention, the distillation zone for the removal of volatile impurity has an upper reflux stage, a lower reboiler stage, and one or more middle distillation stages comprising about 3 to about 12 theoretical stages.

In yet another embodiment of the invention, the dried stream is cooled in a heat exchanger against the volatile impurity stream from the overhead of the distillation zone for the removal of volatile impurity.

These and other embodiments of the present disclosure will be disclosed in further detail herein below.

BRIEF DESCRIPTION OF THE DRAWINGS

The foregoing summary, as well as the following detailed description of the disclosure, will be better understood when read in conjunction with the appended figures. For the purpose of illustrating the disclosure, shown in the figures are embodiments which are presently preferred. It should be understood, however, that the disclosure is not limited to the precise arrangements, examples and instrumentalities shown.

DETAILED DESCRIPTION

The invention disclosed herein relates to a system and method of using the system to separate and purify 1,3-butadiene or isoprene. The process generally comprises the following steps: 1) compression of the gas outlet of the fermenter (composed mostly of carbon dioxide ($CO_2$), water, oxygenates and fermentation byproducts—isoprene or 1,3-butadiene); 2) distillation (optionally) for separation of oxygenates and water; 3) removal of residual water by a drying step by adsorption; and 4) a further distillation step at low temperature for the removal of $CO_2$.

In one aspect of the invention, the process for separating $CO_2$ from 1,3-butadiene or isoprene comprises the steps of compression and distillation, wherein 1,3-butadiene or isoprene are produced from anaerobic fermentation. The composition of the exit gas from the fermenter may be about 35% (by mass) of butadiene or isoprene having essentially no nitrogen or oxygen to pass into the system for separation and purification as shown in FIG. 1.

Figure 1:
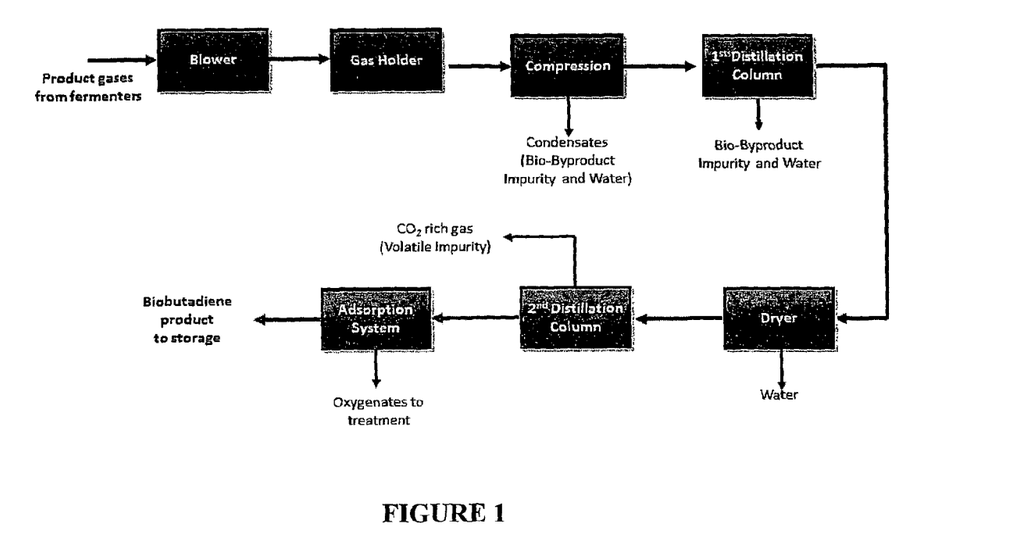
FIG. 1 depicts an overview of an inventive separation process.

In an embodiment shown in FIG. 1, a system and method for biobutadiene and/or isoprene separation and/or purification according to the present disclosure is based on compression and distillation steps. The fermenter off-gas is slightly compressed in the blower and then routed to a gas holder in order to reduce pressure fluctuations downstream. After, the gas is compressed in a compression step. The compression step produces condensates (e.g., the bio-byproduct impurity and water) and a compressed gas. The compressed gas is sent to a first column, where additional bio-byproduct impurities and water are removed.

The overhead product of the first column is passed through a dryer, which typically comprises a desiccant drying system (e.g., a solid adsorbent) to prevent formation of ice of hydrates in the subsequent cryogenic distillation. Examples of solid adsorbents to be used include aluminas, silica, 3 Å molecular sieves, 4 Å molecular sieves, and alumino-silicates.

The overhead product from the dryer is sent to a second column, where volatile impurities (mainly $CO_2$) are removed off the top. The bottom product is purified biobutadiene or isoprene. The second distillation column uses a low temperature refrigerant (e.g., propylene) in the condenser due to low temperatures at the column top.

The purified biobutadiene or isoprene product may be further purified by any suitable means (e.g., by using an adsorption system comprising activated carbon, alumina, silica, Selexsorb®, or a molecular sieve).

Figure 2:
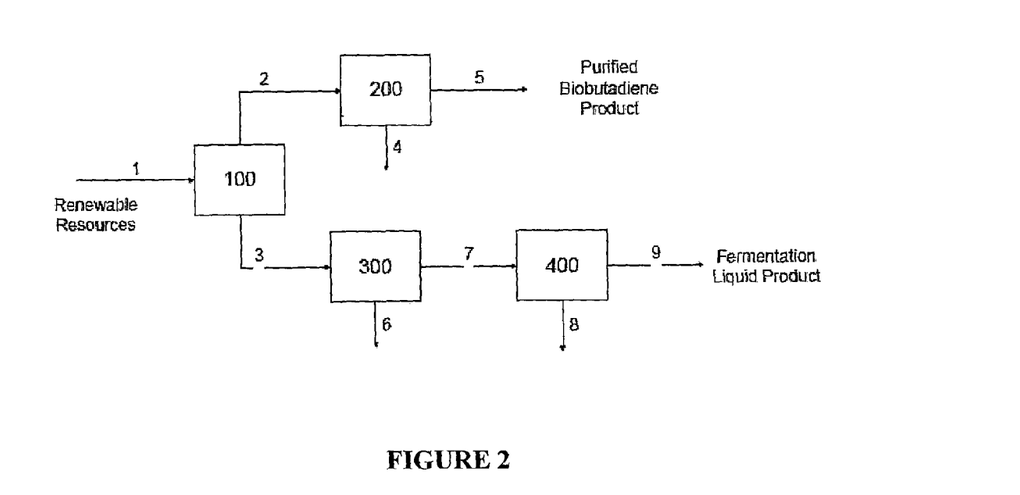
FIG. 2 depicts an overview of an inventive separation process.

Turning to FIG. 2, renewable resources are fed into a fermentor 100 via fluid path 1. After fermentation, the crude liquid product is fed into a microorganism separator 300 via flow path 3. Crude gas products from fermentor 100 are fed to a separator 200 via flow path 2. Separator 200 separates fermentor off-gases from biobutadiene, sending the purified biobutadiene for further use or collection via flow path 5 and the volatile impurities via flow path 4 for additional processing or disposal. The microorganism separator 300 produces a cellular biomass byproduct which exits via flow path 6, and a liquid product which is fed via flow path 7 to a liquid product separator/purifier 400. Purified liquid fermentation product exits the liquid product separator/purifier 400 via flow path 9, while impurities exit the liquid product separator/purifier 400 via flow path 8.

Figure 3:
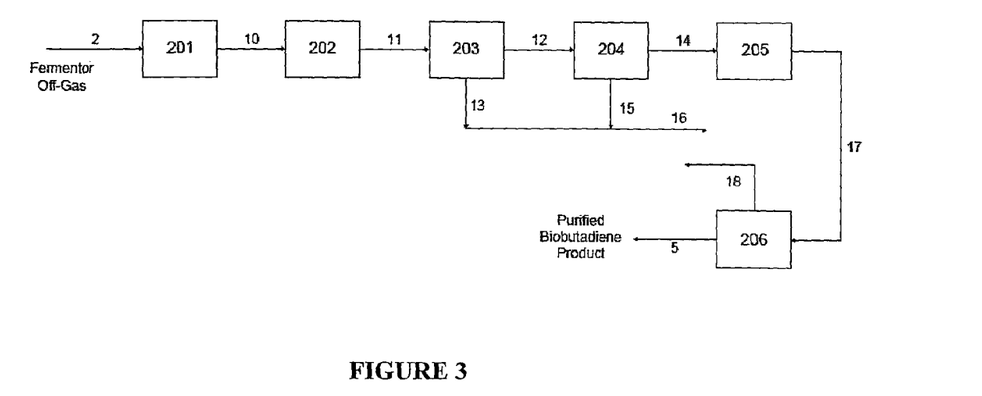
FIG. 3 depicts an overview of a biobutadiene separation process.

Turning now to FIG. 3, fermentor off-gas (e.g., produced by a fermentor as described elsewhere herein including fermentor 100 in FIG. 2) is fed into a blower or fan 201 via flow path 2. From there, the off-gas is fed into a gas holder 202 via flow path 10, and then to a multi-stage compression system 203 via flow path 11. The multi-stage compression system 203 produces a condensate comprising bio-byproduct and water impurity stream which exits via flow path 13, and a compressed gas which is fed into a first distillation zone 204 via flow path 12. The first distillation zone 204 produces additional bio-byproduct impurity and water which exits via flow path 15. In some embodiments, flow paths 13 and 15 combine to form a combined bio-byproduct and water impurity stream 16. First distillation zone 204 also produces an overhead product which is fed into dryer 205 via flow path 14. The dried overhead product is then fed into a second distillation zone 206 via flow path 17. The second distillation zone 206 produces a volatile impurity stream (flow path 18) and a purified biobutadiene or isoprene stream 5.

Figure 4:
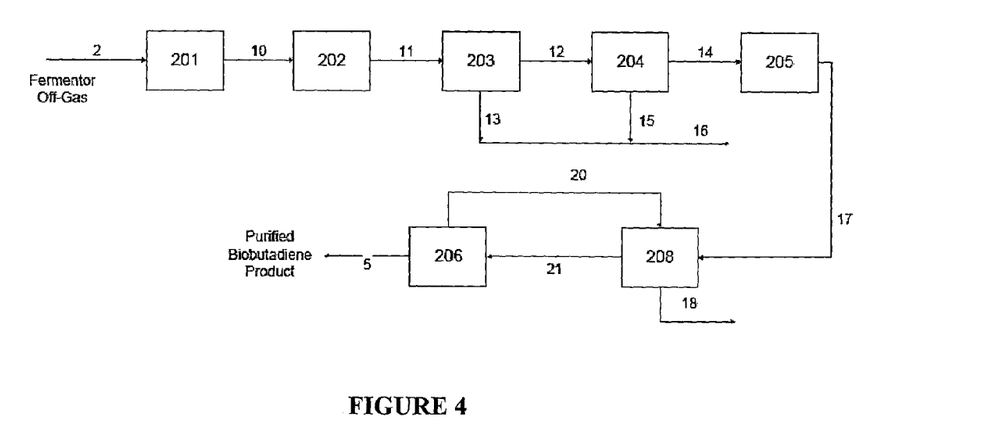
FIG. 4 depicts an overview of a biobutadiene separation process with a heat integration step.

Turning now to FIG. 4, fermentor off-gas (e.g., produced by a fermentor as described elsewhere herein including fermentor 100 in FIG. 2) is fed into a blower or fan 201 via flow path 2. From there, the off-gas is fed into a gas holder 202 via flow path 10, and then to a multi-stage compression system 203 via flow path 11. The multi-stage compression system 203 produces a condensate comprising bio-byproduct and water impurity stream which exits via flow path 13, and a compressed gas which is fed into a first distillation zone 204 via flow path 12. The first distillation zone 204 produces additional bio-byproduct impurity and water which exits via flow path 15. In some embodiments, flow paths 13 and 15 combine to form a combined bio-byproduct and water impurity stream 16. First distillation zone 204 also produces an overhead product which is fed into dryer 205 via flow path 14. The dried overhead product is then fed into a distillation zone feed cooler 208 via flow path 17 before being fed into a second distillation zone 206 via flow path 21. Second distillation zone 206 produces purified biobutadiene or isoprene (flow path 5), and a volatile impurity stream, the latter of which is fed back to the distillation zone feed cooler 208 via flow path 20 to cool the incoming dried overhead product in flow path 17. Volatile impurities produced by the cooler 208 exit via flow stream 18. In embodiments consistent with FIG. 4, the energy consumption is greatly reduced, for example by about 20%.

Figure 5:
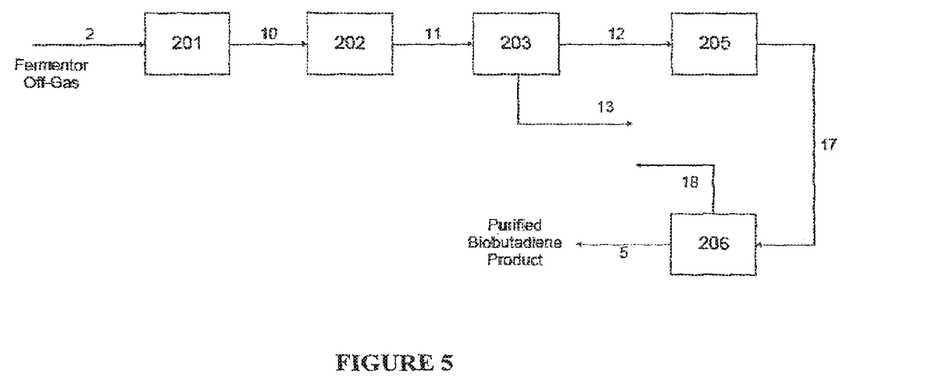
FIG. 5 depicts an overview of an embodiment of a biobutadiene separation process without a first distillation zone to remove impurities and water.

Referring now to FIG. 5, fermentor off-gas (e.g., produced by a fermentor as described elsewhere herein including fermentor 100 in FIG. 2) is fed into a blower or fan 201 via flow path 2. From there, the off-gas is fed into a gas holder 202 via flow path 10, and then to a multi-stage compression system 203 via flow path 11. The multi-stage compression system 203 produces a condensate comprising bio-byproduct and water impurity stream which exits via flow path 13, and a compressed gas which is fed into dryer 205 via flow path 12. The dried overhead product is then fed into a distillation zone 206 via flow path 17. The distillation zone 206 produces a volatile impurity stream (flow path 18) and a purified biobutadiene or isoprene stream 5.

Figure 6:
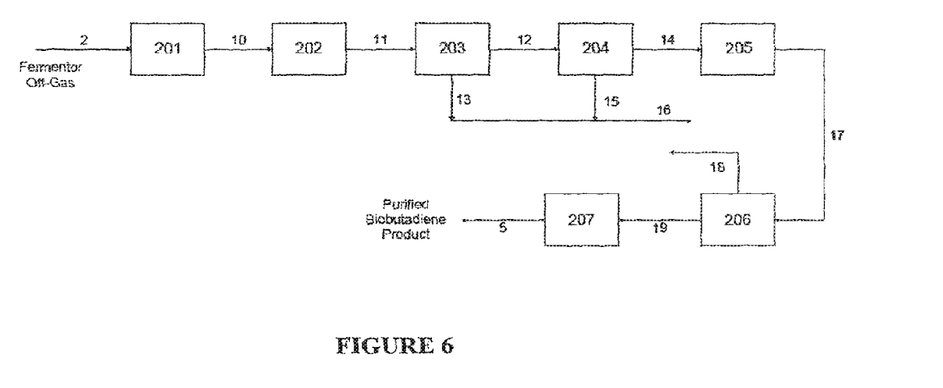
FIG. 6 depicts an overview of a biobutadiene separation process including an adsorption purification system.

Referring now to FIG. 6, fermentor off-gas (e.g., produced by a fermentor as described elsewhere herein including fermentor 100 in FIG. 2) is fed into a blower or fan 201 via flow path 2. From there, the off-gas is fed into a gas holder 202 via flow path 10, and then to a multi-stage compression system 203 via flow path 11. The multi-stage compression system 203 produces a condensate comprising bio-byproduct and water impurity stream which exits via flow path 13, and a compressed gas which is fed into a first distillation zone 204 via flow path 12. The first distillation zone 204 produces additional bio-byproduct impurity and water which exits via flow path 15. In some embodiments, flow paths 13 and 15 combine to form a combined bio-byproduct and water impurity stream 16. First distillation zone 204 also produces an overhead product which is fed into dryer 205 via flow path 14. The dried overhead product is then fed into a second distillation zone 206 via flow path 17. The second distillation zone 206 produces a volatile impurity stream (flow path 18) and a purified biobutadiene or isoprene stream, which is fed into an adsorption purification system 207 via flow path 19. The adsorption purification system 207 can include one or more solid adsorbents such as alumina, silica, activated carbon, Selexsorb®, or a molecular sieve.

In any embodiment described herein, the distillation zones or columns (e.g., distillation zones 204 and/or 206) may include a plurality of theoretical plates. For example, a distillation zone useful in systems and methods disclosed herein may have about 1 to about 25 theoretical plates, or about 3 to about 12 theoretical plates, for example about 1 theoretical plate, about 2 theoretical plates, about 3 theoretical plates about 4 theoretical plates, about 5 theoretical plates, about 6 theoretical plates, about 7 theoretical plates, about 8 theoretical plates, about 9 theoretical plates, about 10 theoretical plates, about 11 theoretical plates, about 12 theoretical plates, about 13 theoretical plates, about 14 theoretical plates, about 15 theoretical plates, about 16 theoretical plates, about 17 theoretical plates, about 18 theoretical plates, about 19 theoretical plates, about 20 theoretical plates, about 21 theoretical plates, about 22 theoretical plates, about 23 theoretical plates, about 24 theoretical plates, or about 25 theoretical plates. In embodiments with two distillation zones, the first distillation zone may include about 1 to about 25 theoretical plates, or about 3 to about 12 theoretical plates, for example 1 theoretical plate, 2 theoretical plates, 3 theoretical plates, 4 theoretical plates, 5 theoretical plates, 6 theoretical plates, 7 theoretical plates, 8 theoretical plates, 9 theoretical plates, 10 theoretical plates, 11 theoretical plates, 12 theoretical plates, 13 theoretical plates, 14 theoretical plates, about 15 theoretical plates, about 16 theoretical plates, about 17 theoretical plates, about 18 theoretical plates, about 19 theoretical plates, about 20 theoretical plates, about 21 theoretical plates, about 22 theoretical plates, about 23 theoretical plates, about 24 theoretical plates, or about 25 theoretical plates, while the second distillation zone may include about 1 to about 25 theoretical plates, or about 3 to about 12 theoretical plates, for example about 1 theoretical plate, about 2 theoretical plates, about 3 theoretical plates, about 4 theoretical plates, about 5 theoretical plates, about 6 theoretical plates, about 7 theoretical plates, about 8 theoretical plates, about 9 theoretical plates, about 10 theoretical plates, about 11 theoretical plates, about 12 theoretical plates, about 13 theoretical plates, about 14 theoretical plates, about 15 theoretical plates, about 16 theoretical plates, about 17 theoretical plates, about 18 theoretical plates, about 19 theoretical plates about 20 theoretical plates, about 21 theoretical plates, about 22 theoretical plates, about 23 theoretical plates, about 24 theoretical plates, or about 25 theoretical plates. In some such embodiments, the first distillation zone has about 4 to about 8 theoretical plates, about 5 to about 7 theoretical plates, or about 6 theoretical plates, and the second distillation zone has about 7 to about 11 theoretical plates, about 8 to 10 theoretical plates, or about 9 theoretical plates.

In any embodiment described herein, the dryer 205 may be any suitable dryer for removing water or water vapor from a gas stream. For example, dryer 205 may include a dessicant drying system that prevents formation of ice of hydrates in subsequent distillation recovery systems. In some embodiments, dryer 205 includes a solid adsorbent such as alumina, silica, alumino-silicates, or a molecular sieve such as a 3 Å and/or a 4 Å molecular sieve.

In some embodiments, the fermentation gas comprises butadiene, propanol, water and carbon dioxide. In some such embodiments, the fermentation gas includes less than about 50%, by weight, of butadiene. In some such embodiments, the fermentation gas comprises less than about 40%, by weight, of butadiene. In some such embodiments, the fermentation gas comprises less than about 36%, by weight, of butadiene. In some such embodiments, the fermentation gas comprises about 35.2%, by weight, of butadiene. In some such embodiments, the fermentation gas includes about 35.2%, by weight, butadiene, about 1.1%, by weight, propanol, about 2.5%, by weight, water and about 61.2%, by weight, carbon dioxide.

Purified butadiene produced according to the present disclosure may include at least about 90%, at least about 91%, at least about 92%, at least about 93%, at least about 94%, at least about 95%, at least about 96%, at least about 97%, at least about 98%, at least about 99%, at least about 99.1%, at least about 99.2%, at least about 99.3%, at least about 99.4%, at least about 99.5%, at least about 99.6%, at least about 99.7%, at least about 99.8%, at least about 99.9%, or about 100.0%, by weight, of butadiene. In some embodiments, the purified butadiene produced according to the present disclosure comprises less than about 5%, less than about 4%, less than about 3%, less than about 2%, less than about 1%, less than about 0.5%, less than about 0.4%, less than about 0.3%, less than about 0.2%, or less than about 0.1%, by weight, of propanol, water and/or carbon dioxide.

Another embodiment the system may include one divided-wall column distillation column where the purified butadiene is withdrawn as a side product.

Another embodiment the system may include the use of a pumparound for heat removal in the cryogenic distillation column.

While the present disclosure is capable of being embodied in various forms, the description below of several embodiments is made with the understanding that the present disclosure is to be considered as an exemplification of the disclosure, and is not intended to limit the disclosure to the specific embodiments illustrated. Headings are provided for convenience only and are not to be construed to limit the disclosure in any manner. Embodiments illustrated under any heading may be combined with embodiments illustrated under any other heading.

Without further description, it is believed that one of ordinary skill in the art may, using the preceding description and the following illustrative examples, make and utilize the agents of the present disclosure and practice the claimed methods. The following working examples are provided to facilitate the practice of the present disclosure, and are not to be construed as limiting in any way the remainder of the disclosure.

EXAMPLES

Example 1: System for Separation of Butadiene

In this example, a fermentor off-gas was processed into a purified biobutadiene product using a system according to FIG. 3. The fermentor off-gas included 35.2 wt. % butadiene, 1.1 wt. % propanol, 2.5 wt. % water, and 61.2 wt. % carbon dioxide (Table 1). The compressor 203 was a three-stage compressor processing 53,734 kg per hour at 65° C. and 1.5 bar (incoming), and produced a gas stream flowing at 52,878 kg per hour at 122° C. and 16.5 bar. First distillation column 204 included seven theoretical plates and a partial condenser, but no reboiler. Compressed gas entered column 204 at the bottom. Overhead product exited the top of column 204 at 91° C. and 15.5 bar pressure at a rate of 1,277 kg per hour and included no detectable propanol or water. The condensate included 4.0 wt. % butadiene, 43.3 wt. % propanol, 52.1 wt. % water and 0.6 wt. % carbon dioxide After dryer 205, the composition entered second distillation column 206 at the third of nine theoretical steps at 44° C. and 15.5 bar. The overhead gas exiting column 206 included 99.9 wt. % carbon dioxide and 0.1 wt. % butadiene, while the condensate included 100.0 wt. % butadiene at 73° C.

TABLE 1

Composition of Butadiene Stream During Processing.

| Component | Initial | After Compressor 203 | After First Distillation Column 204 | After Dryer 205 | Final |
| --- | --- | --- | --- | --- | --- |
| Butadiene | 35.2 wt. % | 35.8 wt. % | 36.5 wt. % | 36.5 wt. % | 100.0 wt. % |
| Propanol | 1.1 wt. % | 0.9 wt. % | 0 wt. % | 0 wt. % | 0 wt. % |
| Water | 2.5 wt. % | 1.2 wt. % | 0 wt. % | 0 wt. % | 0 wt. % |
| Carbon Dioxide | 61.2 wt. % | 62.1 wt. % | 63.5 wt. % | 63.5 wt. % | 0 wt. % |

Example 2: System for Separation of Butadiene

In this example, a fermentor off-gas was processed into a purified biobutadiene product using a system according to FIG. 4. The fermentor off-gas included 35.2 wt. % butadiene, 1.1 wt. % propanol, 2.5 wt. % water, and 61.2 wt. % carbon dioxide (Table 2). The compressor 203 was a three-stage compressor processing 53,734 kg per hour at 65° C. and 1.5 bar (incoming), and produced a gas stream flowing at 52,878 kg per hour at 122° C. and 16.5 bar. First distillation column 204 included six theoretical plates and a partial condenser, along with a reboiler for re-processing condensate. Compressed gas entered column 204 at the fifth stage. Overhead product exited the top of column 204 at 91° C. and 15.5 bar pressure at a rate of 1,277 kg per hour and included no detectable propanol or water. The condensate included 4.0 wt. % butadiene, 43.3 wt. % propanol, 52.1 wt. % water and 0.6 wt. % carbon dioxide After dryer 205, the composition entered second distillation column 206, at the third of nine theoretical steps at 44° C. and 15.5 bar. Second column 206 included a reboiler. Carbon dioxide-rich gas exiting second column 206 (at −40° C.) included 99.9 wt. % carbon dioxide and 0.1 wt. % butadiene and was used to cool the incoming gas feed from dryer 205 via heat exchange. Energy consumption of the second column was reduced by about 20% due to incorporation of the heat exchange. The condensate exiting second column 206 included 100.0 wt. % butadiene at 73° C.

TABLE 2

Composition of Butadiene Stream During Processing.

| Component | Initial | After Compressor 203 | After First Distillation Column 204 | After Dryer 205 | Final |
|---|---|---|---|---|---|
| Butadiene | 35.2 wt. % | 35.8 wt. % | 36.5 wt. % | 36.5 wt. % | 100.0 wt. % |
| Propanol | 1.1 wt. % | 0.9 wt. % | 0 wt. % | 0 wt. % | 0 wt. % |
| Water | 2.5 wt. % | 1.2 wt. % | 0 wt. % | 0 wt. % | 0 wt. % |
| Carbon Dioxide | 61.2 wt. % | 62.1 wt. % | 63.5 wt. % | 63.5 wt. % | 0 wt. % |

Example 3: System for Separation of Butadiene

In this example, a fermentor off-gas was processed into a purified biobutadiene product using a system according to FIG. 5. The fermentor off-gas included 35.2 wt. % butadiene, 1.1 wt. % propanol, 2.5 wt. % water, and 61.2 wt. % carbon dioxide (Table 3). The compressor 203 was a three-stage compressor processing 53,734 kg per hour at 65° C. and 1.5 bar (incoming), and produced a gas stream flowing at 52,878 kg per hour at 122° C. and 16.5 bar. The aqueous bio-byproduct exited compressor 203 at 60° C. at 5.7 bar, and included 0.8 wt. % butadiene, 9.3 wt. % propanol, 86.5 wt. % water, and 3.4 wt. % carbon dioxide. Compressed gas entered dryer 205 at 109° C. and 11.0 bar at a flow rate of 53,096 kg per hour. The dried gas stream entered distillation column 206 at the third of nine theoretical steps. Distillation column 206 included a reboiler. Carbon dioxide-rich gas exited column 206 at −40° C. and included 99.9 wt. % carbon dioxide and 0.1 wt. % butadiene. The condensate exiting column 206 included 97.2 wt. % butadiene and 2.8 wt. % propanol at 74° C., and entered adsorption purification system 207. After processing in the adsorbent purification system 207, the final product included 100.0 wt. % butadiene at 73° C. and 10.0 bar.

TABLE 3

Composition of Butadiene Stream During Processing.

| Component | Initial | After Compressor 203 | After Dryer 205 | After Distillation Column 206 | Final |
|---|---|---|---|---|---|
| Butadiene | 35.2 wt. % | 35.6 wt. % | 36.2 wt. % | 97.2 wt. % | 100.0 wt. % |
| Propanol | 1.1 wt. % | 1.0 wt. % | 1.0 wt. % | 2.8 wt. % | 0 wt. % |
| Water | 2.5 wt. % | 1.4 wt. % | 0 wt. % | 0 wt. % | 0 wt. % |
| Carbon Dioxide | 61.2 wt. % | 61.9 wt. % | 62.8 wt. % | 0 wt. % | 0 wt. % |

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present disclosure. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the disclosure are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the disclosure (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the disclosure and does not pose a limitation on the scope of the disclosure otherwise claimed. No language in the specification should be construed as indicating any non-claimed element essential to the practice of the disclosure.

Groupings of alternative elements or embodiments of the disclosure disclosed herein are not to be construed as limitations. Each group member can be referred to and claimed individually or in any combination with other members of the group or other elements found herein. It is anticipated that one or more members of a group can be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this disclosure are described herein, including the best mode known to the inventors for carrying out the disclosure. Of course, variations on these described embodiments will become apparent to those of ordinary skill in the art upon reading the foregoing description. The inventor expects skilled artisans to employ such variations as appropriate, and the inventors intend for the disclosure to be practiced otherwise than specifically described herein. Accordingly, this disclosure includes all modifications and equivalents of the subject matter recited in the claims appended hereto as permitted by applicable law. Moreover, any combination of the above-described elements in all possible variations thereof is encompassed by the disclosure unless otherwise indicated herein or otherwise clearly contradicted by context.

Specific embodiments disclosed herein can be further limited in the claims using consisting of or and consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the disclosure so claimed are inherently or expressly described and enabled herein.

It is to be understood that the embodiments of the disclosure disclosed herein are illustrative of the principles of the present disclosure. Other modifications that can be employed are within the scope of the disclosure. Thus, by way of example, but not of limitation, alternative configurations of the present disclosure can be utilized in accordance with the teachings herein. Accordingly, the present disclosure is not limited to that precisely as shown and described.

While the present disclosure has been described and illustrated herein by references to various specific materials, procedures and examples, it is understood that the disclosure is not restricted to the particular combinations of materials and procedures selected for that purpose. Numerous variations of such details can be implied as will be appreciated by those skilled in the art. It is intended that the specification and examples be considered as exemplary, only, with the true scope and spirit of the disclosure being indicated by the following claims. All references, patents, and patent applications referred to in this application are herein incorporated by reference in their entirety.

The invention claimed is:

1. A method of separating and purifying a conjugated diolefin produced by fermentation under anaerobic conditions from a fermenter off-gas comprising the steps of:
   a) obtaining a fermenter off-gas stream comprising the conjugated diolefin, a volatile impurity, a bio-byproduct impurity and water;
   b) compressing the fermenter off-gas stream in a multi-stage compression system to produce a compressed stream;
   c) feeding the compressed stream into a first distillation zone having an upper reflux stage, middle distillation stages and a lower reboiler stage, wherein the bio-byproduct impurity and the water are removed from the lower reboiler stage;
   d) drying an overhead vapor stream produced by the first distillation zone with an adsorbent to produce a dried stream;
   e) feeding the dried stream into a second distillation zone having an upper reflux stage, middle distillation stages and a lower reboiler stage, wherein the volatile impurity is removed from the upper reflux stage; and
   f) collecting a purified liquid conjugated diolefin from the lower reboiler stage of the second distillation zone.

2. The method of claim 1, wherein the conjugated diolefin comprises a compound selected from the group consisting of 1,3-butadiene and isoprene.

3. The method of claim 1, wherein the volatile impurity comprises a compound selected from the group consisting of $H_2O$ and $CO_2$.

4. The method of claim 3, wherein the volatile impurity comprises about 30 to about 80 mol % $CO_2$, and about 1 to about 20 mol % $H_2O$.

5. The method of claim 4, wherein the volatile impurity comprises about 45 to about 70 mol % $CO_2$.

6. The method of claim 1, wherein the bio-byproduct impurity comprises a polar impurity.

7. The method of claim 1, wherein the bio-byproduct impurity comprises a compound selected from the group consisting of ethanol, acetone, methanol, acetaldehyde, methacrolein, methyl vinyl ketone, 3-methylfuran, 2-methyl-2-vinyloxirane, cis- and trans-3-methyl-1,3-pentadiene, a C5 prenyl alcohol (such as 3-methyl-3-buten-1-ol or 3-methyl-2-buten-1-ol), 2-heptanone, 6-methyl-5-hepten-2-one, 2,4,5-trimethylpyridine, 2,3,5-trimethylpyrazine, citronellal, methanethiol, methyl acetate, 1-propanol, diacetyl, 2-butanone, 2-methyl-3-buten-2-ol, ethyl acetate, 2-methyl-1-propanol, 3-methyl-1-butanal, 3-methyl-2-butanone, 1-butanol, 2-pentanone, 3-methyl-1-butanol, ethyl isobutyrate, 3-methyl-2-butenal, butyl acetate, 3-methylbutyl acetate, 3-methyl-3-buten-1-yl acetate, 3-methyl-2-buten-1-yl acetate, (E)-3,7-dimethyl-1,3,6-octatriene, (Z)-3,7-dimethyl-1,3,6-octatriene, (E E)-3,7,11-trimethyl-1,3,6,10-dodecatetraene, (E)-7,11-dimethyl-3-methylene-1,6,10-dodecatriene, 3-hexen-1-ol, 3-hexen-1-yl acetate, limonene, geraniol (trans-3,7-dimethyl-2,6-octadien-1-ol), and citronellol (3,7-dimethyl-6-octen-1-ol).

8. The method of claim 1, wherein an amount of bio-byproduct impurity relative to an amount of the conjugated diolefin in the fermenter off-gas stream is greater than about 0.01% by weight.

9. The method of claim 8, wherein the amount of bio-byproduct impurity relative to the amount of the conjugated diolefin in the fermenter off-gas stream is greater than about 0.5% by weight.

10. The method of claim 1, wherein the purified liquid conjugated diolefin is further purified with an adsorption system.

11. The method of claim 10, wherein the adsorption system comprises an adsorbent selected from the group consisting of activated carbon, alumina, silica; and combinations thereof.

12. The method of claim 1, wherein the purified liquid conjugated diolefin composition has a purity greater than about 90% la weight.

13. The method of claim 12, wherein the purified liquid conjugated diolefin composition has a purity greater than about 99% la weight.

14. The method of claim 1, wherein a compressed fermenter off-gas stream exits the multi-stage compression system at a pressure of from about 6 bar to about 30 bar.

15. The method of claim 14, wherein the compressed fermenter off-gas stream exits the multi-stage compression system at a pressure of from about 9 bar to about 18 bar.

16. The method of claim 1, wherein the first distillation zone has an upper reflux stage, a lower reboiler stage, and middle distillation stages comprising about 1 to about 25 theoretical stages.

17. The method of claim 16, wherein the first distillation zone has an upper reflux stage, a lower reboiler stage, and middle distillation stages comprising about 3 to about 12 theoretical stages.

18. The method of claim 17, wherein the first distillation zone consists of an upper reflux stage and middle distillation stages comprising about 3 to about 12 theoretical stages.

19. A method of separating and purifying a conjugated diolefin produced by fermentation under anaerobic conditions from a fermenter off-gas comprising the steps of:
   a) obtaining a fermenter off-gas comprising the conjugated diolefin, a volatile impurity, a bio-byproduct impurity and water;
   b) compressing the fermenter off-gas in a multi-stage compression system to form a condensate;
   c) drying the condensate to produce a dried stream;
   d) feeding the dried stream into a distillation zone having an upper reflux stage, middle distillation stages and a lower reboiler stage, wherein the volatile impurity is removed from the upper reflux stage; and
   e) collecting a purified liquid conjugated diolefin from the lower reboiler stage of the distillation zone.

20. The method of claim 19, wherein the distillation zone has an upper reflux stage, a lower reboiler stage, and middle distillation stages comprising about 1 to about 25 theoretical stages.

21. The method of claim 20, wherein the distillation zone has an upper reflux stage, a lower reboiler stage, and middle distillation stages comprising about 3 to about 12 theoretical stages.

22. The method of claim 19, wherein the dried stream is cooled in a heat exchanger against the volatile impurity from the upper reflux stage of the distillation zone for the removal of volatile impurity.

* * * * *